United States Patent
Glinsky et al.

[11] Patent Number: 5,827,265
[45] Date of Patent: Oct. 27, 1998

[54] INTRALUMINAL TISSUE WELDING FOR ANASTOMOSIS

[75] Inventors: Michael Glinsky, Livermore; Richard London, Orinda; George Zimmerman, Lafayette, all of Calif.; Steven Jacques, Portland, Oreg.

[73] Assignee: Regents of the University of California, Oakland, Calif.

[21] Appl. No.: 801,224

[22] Filed: Feb. 19, 1997

Related U.S. Application Data

[63] Continuation-in-part of Ser. No. 598,044, Feb. 7, 1996, abandoned.

[51] Int. Cl.⁶ .............................. A61B 17/36; A61F 2/06
[52] U.S. Cl. ............................................. 606/8; 623/12
[58] Field of Search ................ 604/21, 96; 606/194, 606/198, 2, 7, 8, 13, 14, 15, 16, 17; 623/1, 12

[56] References Cited

U.S. PATENT DOCUMENTS

| | | | |
|---|---|---|---|
| 4,633,870 | 1/1987 | Sauer | 606/8 |
| 4,892,098 | 1/1990 | Sauer | 606/8 |
| 5,092,841 | 3/1992 | Spears | 604/96 |
| 5,207,670 | 5/1993 | Sinofsky | 606/8 |
| 5,254,113 | 10/1993 | Wilk | 606/8 |
| 5,290,278 | 3/1994 | Anderson | 606/8 |
| 5,304,171 | 4/1994 | Gregory et al. | 606/15 |
| 5,364,389 | 11/1994 | Anderson | 606/8 |
| 5,417,653 | 5/1995 | Sahota et al. | 606/7 |
| 5,468,239 | 11/1995 | Tanner et al. | 606/17 |
| 5,505,725 | 4/1996 | Samson | 606/7 |
| 5,522,882 | 6/1996 | Gaterud et al. | 623/1 |
| 5,575,815 | 11/1996 | Slepian et al. | 623/1 |
| 5,591,199 | 1/1997 | Porter et al. | 623/1 |
| 5,662,712 | 9/1997 | Pathak et al. | 623/12 |

OTHER PUBLICATIONS

Modeling of Endovascular Patch Welding Using The Computer Program (LATIS), Michael E. Glinsky (LLNL), Steven L. Jacques (Univ. of Texas), Proceedings of Laser--Tissue Interaction VI, vol. 2391, pp. 262–272 (1995).

Computer Modeling of Endovascular Patch Welding Using Temperature Feedback, Glinsky et al., Proceedings of Medical Applications of Lasers III, vol. 2623, pp. 349–358 (1995.

*Primary Examiner*—Jennifer Bahr
*Assistant Examiner*—Sonya Harris-Ogugua
*Attorney, Agent, or Firm*—Daryl S. Grzybicki

[57] ABSTRACT

A method and device are provided for performing intraluminal tissue welding for anastomosis of a hollow organ. A retractable catheter assembly is delivered through the hollow organ and consists of a catheter connected to an optical fiber, an inflatable balloon, and a biocompatible patch mounted on the balloon. The disconnected ends of the hollow organ are brought together on the catheter assembly, and upon inflation of the balloon, the free ends are held together on the balloon to form a continuous channel while the patch is deployed against the inner wall of the hollow organ. The ends are joined or "welded" using laser radiation transmitted through the optical fiber to the patch. A thin layer of a light-absorbing dye on the patch can provide a target for welding. The patch may also contain a bonding agent to strengthen the bond. The laser radiation delivered has a pulse profile to minimize tissue damage.

15 Claims, 3 Drawing Sheets

INTRALUMINAL TISSUE WELDING FOR ANASTOMOSIS

RELATED APPLICATION

This application is a continuation-in-part of U.S. Ser. No. 08/598,044, filed Feb. 7, 1996, which is now abandoned.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

This invention relates to a method for performing an anastomosis using a retractable catheter assembly that facilitates tissue welding of hollow organs.

2. Description of Related Art

Endovascular welding of patches or stents is used to close aneurysms, reinforce vessel walls, cover vessel walls after angioplasty or metal stent deployment, and to achieve anastomosis. Anastomosis is a procedure to restore a continuous channel between hollow organs that have been severed or separated. Anastomosis is often used to treat blocked or narrowed blood vessels (i.e., stenosis). A continuous channel can be accomplished by removing part of the blocked organ and using a biocompatible patch or graft to re-form the organ. The patches or grafts must somehow be attached to the organ walls, and tissue welding and soldering have been suggested as means to accomplish this attachment.

In the tissue welding of a patch, the organ wall and patch are heated to a temperature that is high enough for a long enough period of time to cause the organ wall and patch to join. Different mechanisms have been proposed for how this bonding occurs. To prevent or limit tissue damage or necrosis, the area that is heated should be minimized. Laser radiation has been used to control the zone of damage and to "weld" the patch to the organ wall.

An additional challenge exists when attempting to perform tissue welding during cardiovascular anastomosis of bypass grafts on a beating heart in a coronary artery bypass operation. This procedure must be done quickly since the heart is working and cannot be starved of its oxygen supply. The conventional practice is to use staples or many small sutures to secure the graft or patch, which requires great precision and is time-consuming. Tissue welding is a better procedure; however, the instruments (including a laser light source, a patch, and patch placement device) must somehow be moved along with the heart as it beats while the anastomosis is performed. The present invention addresses this problem of performing anastomosis with a beating heart and also avoids the use of many small sutures or staples and the time needed to place them.

SUMMARY OF THE INVENTION

The present invention is a method and device for performing intraluminal tissue welding for anastomosis. The anastomosis is performed on two free ends of a hollow organ that has been severed, typically to remove a blockage from the lumen of the hollow organ. A retractable catheter assembly is delivered through the hollow organ to the site of the anastomosis, where the assembly comprises a catheter connected to an optical fiber having an inflatable balloon mounted thereon, with a biocompatible patch positioned circumferentially around the balloon. The catheter assembly is positioned between the free ends, and the free ends are brought together. Upon inflation of the balloon, two goals are accomplished: the free ends of the hollow organ are held together on the balloon to form a continuous channel, and the patch is deployed, pressing against the inner wall of the hollow organ.

The two free ends are joined by welding the patch to the inner wall of the hollow organ using laser radiation. Laser light is transmitted through the optical fiber and the balloon to the patch, which reacts to the laser light by forming a bond between the organ wall and the patch. The patch may include a thin layer of a light-absorbing dye on the side of the patch being welded to the organ wall, where the dye preferentially absorbs the light and provides a "target" for welding. The patch may also contain a bonding agent to strengthen the weld, such as a polymer that forms a mechanical bond between the patch and tissue when heated.

To minimize tissue damage, the laser light has a pulse structure with a pulse length that is substantially equal to the time for the laser energy to diffuse across the region over which the laser energy is deposited, and a delay time between pulses that is substantially equal to the time needed for the heated region to cool. In the present context, "substantially equal" includes a difference of a factor of two.

DETAILED DESCRIPTION OF THE INVENTION

The present invention is a method and device for anastomosis of hollow organs. The invention may be used on a variety of hollow organs in a body space where an opening must be established in a blocked or narrow passage, such as in an artery or vein, a ureter or duct, trachea, bronchus, or in the gastrointestinal tract. The method is particularly well suited for blocked coronary arteries in bypass operations.

Figure 1:
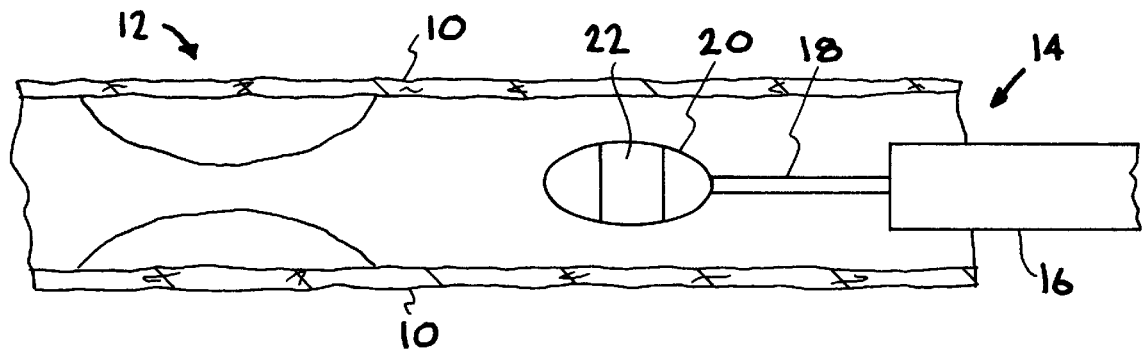
FIG. 1 shows a narrowed vessel and a catheter assembly in the vessel.

In one embodiment of the present invention, anastomosis of an artery is performed. FIG. 1 shows a longitudinal cross-section of an artery passage 10 that has narrowed (exhibiting stenosis), for which removal of the narrowed section 12 and anastomosis of the two free ends of the artery is required. According to the present invention, a retractable catheter assembly 14 is inserted into the vessel 10 and placed next to the site for the anastomosis. The catheter assembly includes a catheter 16 that is connected on one end to an optical fiber 18, upon which is mounted at least one inflatable balloon 20. The balloon 20 can be inflated to touch (and stretch) the walls of the artery 10 to form a seal with the artery walls. The catheter 16 is defined as a tube of appropriate dimensions for the lumen being treated, which could range in diameter from microns to centimeters.

Figure 2:
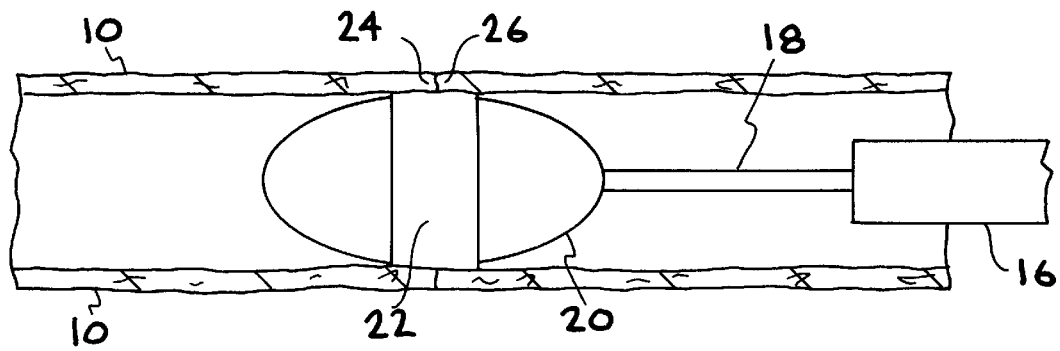
FIG. 2 shows an intraluminal anastomosis using laser welded patches.

Balloons are typically used in angioplasty to open a passageway, but in this invention, the balloons are used instead to deploy a biocompatible patch and hold the two cut ends of the artery in place while the patch is welded to the artery wall. The patch 22 (also called a "collar") to be welded to the artery is wound circumferentially around the uninflated balloon so that when the balloon is inflated, the patch is deployed against the wall of the artery. FIG. 2 shows the cross-section of the vessel 10 with the narrowed section now removed. The free ends 24,26 of the artery 10 are juxtaposed and held together on the inflated balloon 22 with the patch 22 deployed against the artery wall, overlapping the free ends 24,26.

The patch is made from a biomaterial (e.g., collagen) that is compatible with the arterial tissue and has enough strength to maintain the integrity of the wall after welding and not be ruptured by arterial pressure. The patch itself may have a thin layer of absorbing dye (such as indocyanine green) on the side facing the artery wall that absorbs a certain wavelength of light during tissue welding. The patch may also include a layer with a bonding agent such as albumin or a special form of collagen optimized to maximize the bond strength when the patch is welded to the artery wall. In yet another embodiment, the patch may contain a layer of a chemical material that polymerizes upon exposure to laser light to form a mechanical bond between the patch and arterial wall.

Figure 3:
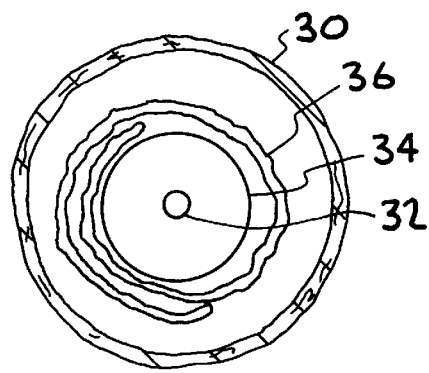
FIG. 3 is a cross-sectional view of a catheter assembly in a vessel.

To activate the dyes or polymers and to perform the tissue welding, the catheter assembly is equipped with means for transmitting laser light to the site of the dye or polymer, typically an optical fiber. FIG. 3 shows a radial cross-section of the balloon end of the catheter assembly inside a vessel 30, showing the configuration of an optical fiber 32, an inflatable balloon 34, and a patch 36 mounted circumferentially around the balloon 34 such that the patch 36 uncurls when the balloon 34 is inflated. The patch 36 has a thin layer of light-absorbing dye on the side next to the vessel 30. The catheter assembly may be surrounded with a protective sheath (not shown) for deployment inside the patient's body, so the catheter assembly can be guided more easily to the blockage, preventing damage to the arterial walls.

In practice, the catheter assembly is guided to the blocked artery, and the artery is cut on both sides of the blockage. To stop the blood flow to this part of the artery, clamps or inflated balloons may be used to form a seal with the arterial wall. The catheter assembly with the balloon and patch are positioned so that the balloon is half in and half out of one end of the cut artery. The other end of the cut artery is slipped over the other half of the balloon so that the inflated balloon holds the two cut ends of the artery together, as shown in FIG. 2. When the balloon is inflated, the patch presses against the artery wall.

Laser light is sent down the optical fiber and is diffused throughout the balloon, giving reasonably uniform illumination to the patch. The laser light is preferably pulsed so that the zone of thermal damage to the nearby vessel wall is minimized. If the patch has been coated with a thin outer layer of dye, then the laser wavelength is chosen so that the light is absorbed by the dye. The energy heats up the thin layer on the patch and the adjacent vessel wall, which bonds or "welds" the patch to the artery wall. The patch serves as a means of joining the tissue. The thin layer of dye on the patch minimizes the zone of damage since this layer at the patch-artery interface preferentially absorbs the laser energy and is heated. A thin layer of dye, thus, is preferable to a patch permeated with the dye.

A layer of bonding agent may also be present on the patch to facilitate or strengthen the bond, or a chemical that polymerizes upon exposure to the laser light can be used to form a mechanical bond to the arterial wall. The layer of dye or bonding agent or polymer could also be applied directly to the arterial wall in addition to or instead of the coated patch, although coating the patch with the chemical layer may be easier. Once the patch is bonded to the wall and secure, the balloon(s) can be deflated, the clamp(s) released, and the catheter assembly retracted.

Figure 4:
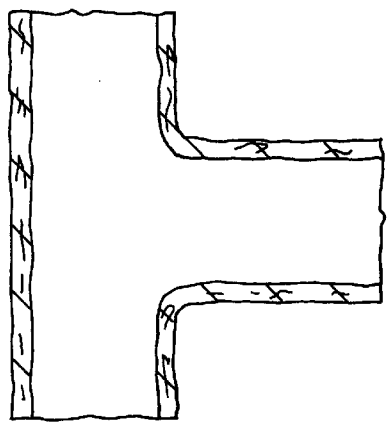
FIG. 4 shows a side-to-end anastomosis.
Figure 5:
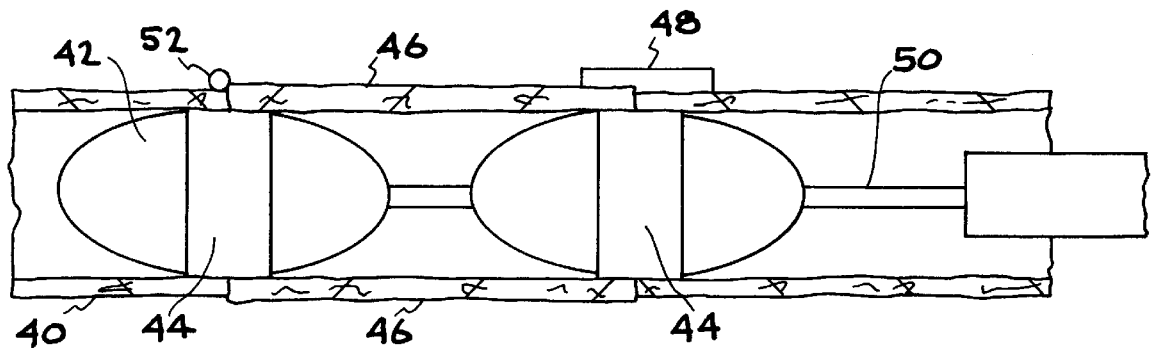
FIG. 5 shows an anastomosis using a graft and laser welding.

There are numerous alternative embodiments to this technique. The present technique is easily applied to end-to-end anastomoses, as exemplified in FIG. 2, but can be used in a side-to-end anastomosis, as illustrated in FIG. 4. In another embodiment of the invention, more than two free ends of a hollow organ can be welded. FIG. 5 shows a vessel 40 with two pairs of vessel ends being welded together using at least two balloons 42 and two patches 44. The patches 44 help to secure a graft 46 of living tissue or prosthetic material, and if desired, a patch 48 may also be implanted on the outer wall of the vessel 40.

The patches or the vessel wall typically have a layer of dye or a bonding agent, and the patches 44 are welded to the vessel wall as laser light is transmitted through the optical fiber 50 and absorbed at the patches 44. Anastomosis may be aided using a biological "solder" 52 (e.g., albumin-ICG) that is applied by an external applicator to the graft-artery boundary. Laser light transmitted through the optical fiber 50 heats the solder 52, which acts as a light-activated "glue" to bond the graft 46 directly to the vessel 40.

Although the laser light can also be introduced from outside the vessel, a clear advantage of the present method is that the procedure is minimally invasive since the source of laser energy is within the vessel itself and moves along with any movement of the vessel. An internal laser source is ideal for coronary bypass operations, where time is critical and the movement of the beating heart makes an outside laser source problematic.

The pulse structure of the laser light used for patch welding must be chosen carefully to minimize or prevent damage to the hollow organ being welded. The effect of pulsed laser radiation with temperature feedback on endovascular patch welding has been studied using computer simulations. See Glinsky et al., "Computer modeling of endovascular patch welding using temperature feedback", *Proceedings of Medical Applications of Lasers III*, Vol. 2623, pp. 349–358 (1995) and Glinsky et al., "Modeling of endovascular patch welding using the computer program LATIS", *Proceedings of Laser-Tissue Interaction IV*, Vol. 2391, pp. 262–272 (1995). These studies, which are hereby incorporated by reference, show that it is possible to control the zone of damage using pulsed laser irradiation.

The minimum size of the damage zone is determined by the thickness of the layer over which the laser energy is deposited. A minimum zone of damage can be achieved using a pulse length that is substantially equal (i.e., within a factor of two) to the time the energy diffuses across the layer. The delay time between pulses is determined by the time it takes for the heated tissue layer to cool down. The delay time is substantially equal (i.e., within a factor of two) to the cooling time.

The conclusion that pulsed energy delivery can lead to a controlled zone of damage is based on the exponential nonlinearity of the reaction rate, given by the Arrenhius equation (where $\Delta H$ is the enthalpy of reaction and $\Delta S$ is the entropy of reaction):

$$k(T) = \frac{k_s}{h} T \exp\left(\frac{-\Delta H}{RT} + \frac{\Delta S}{R}\right). \quad [1]$$

If energy is delivered to a volume on a time scale that is greater than or equal to the time for energy to thermally diffuse across the layer, then the temperature will decay as $L^{-d}$, where d is the dimensionality of the volume over which the heat is spreading (d=1, 2, and 3 for a slab, cylinder, and sphere respectively), and L is the distance across the volume. For thermal diffusion, L varies with $t^{1/2}$, where t is the time since the energy was deposited. The number of undamaged molecules $N_u$ evolves according to the equation:

$$\frac{dN_u}{dt} = -k(T)N_u.$$

The number of undamaged molecules evolves as $N_{tot} \exp(-\Omega)$, where $N_{tot}$ is the initial number of molecules and $\Omega = \int k\, dt$ is the damage index. Using equation [1], the scaling of $\Omega$ with L is given by $$\Omega \propto L^{2-d} e^{-(L/L_o)^d},$$

where $L_o$ is a constant, the factor $L^2$ is contributed by $\int dt$, and the factor $L^{-d}e^{-(L/L_o)^d}$ is contributed by the reaction rate. For the small length scales of interest, not enough damage can be done with one pulse, so multiple pulses must be applied to accumulate the damage. The pulses must be separated by enough time and the average temperature kept low enough so that the tissue will not become damaged over the course of treatment.

Figure 6A:
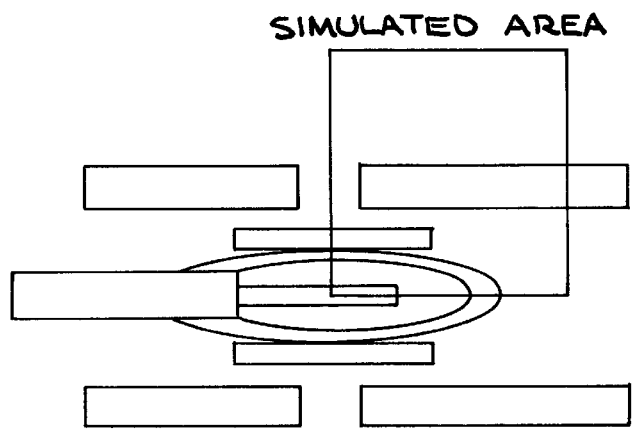
FIG. 6 shows the geometry of the computer simulated area used to determine optimal laser pulse profiles.
Figure 6B:
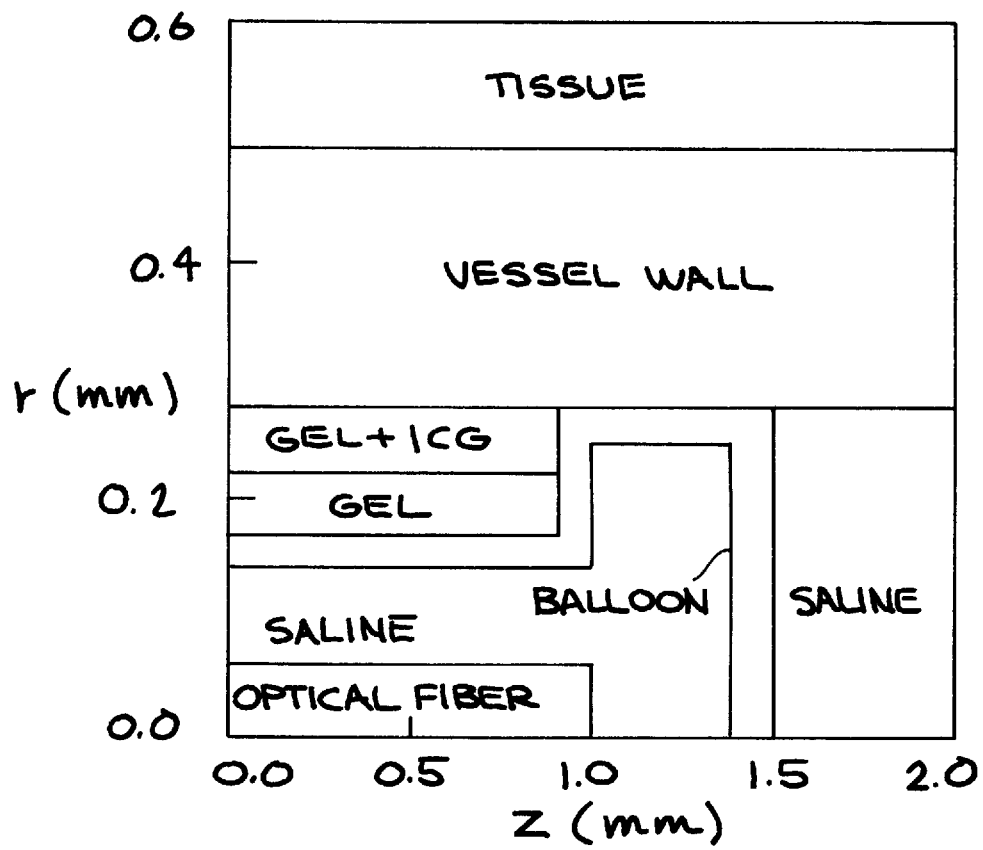
Figure 7:
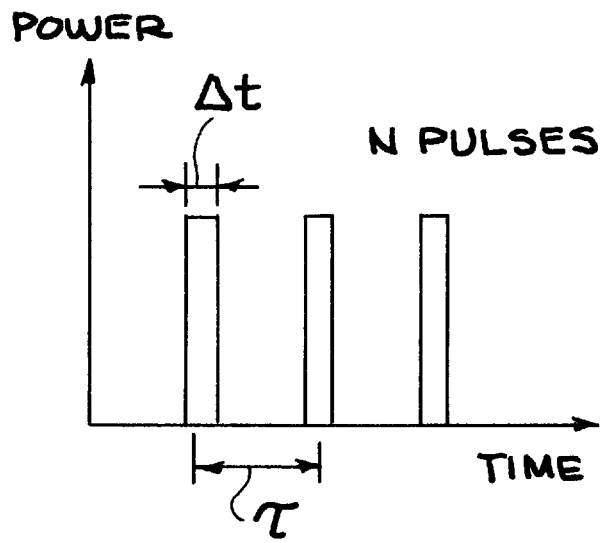
FIG. 7 shows a laser pulse profile.

A summary of the results of computer simulations for soft tissue is given in Table I, where $\Delta t$ is the pulse length, N is the number of pulses, t is the pulse delay, $N_t$ is the total treatment time, and $\Delta x$ is the depth of the zone of damage. The computer simulations were done using the geometry shown in FIG. 6A and FIG. 6B. The laser pulse profile is shown in FIG. 7, which consist of a train of square pulses of length $\Delta t$ separated by delay t. Further details concerning the computer simulation are given in the previously cited Glinsky et al. references.

TABLE I

| $\Delta t$ (ms) | N pulses | t (sec) | $N_t$ (min) | $\Delta x$ (μm) |
|---|---|---|---|---|
| 20 | 2865 | 0.22 | 10.5 | 110 |
| 60 | 595 | 0.48 | 4.8 | 66 |
| 200 | 124 | 1.3 | 2.7 | 76 |
| 600 | 33 | 3 | 1.6 | 96 |
| 2000 | 9 | 7.2 | 1.1 | 128 |
| 6000 | 3 | 16 | 0.8 | 164 |

The optimal pulse length minimizes the total treatment time needed to weld a patch to the wall, while keeping the thickness of the damaged tissue to less than 100 μm. For example, using a 100 μm thickness collagen patch with a 60 μm layer of light-absorbing indocyanine green (ICG) dye on the side next to the wall, the zone of damage can be limited to a depth of 96 μm by applying 33 600 ms pulses over 1.6 minutes. In this way, the minimum damage zone is about the thickness of the patch that is heated by the laser. If a longer treatment time is allowed, the numbers in Table I can be interpolated so that for a damage zone depth still less than 100 μm, 100 ms pulses with a delay time of about 1 second could be used. To ensure that tissue damage is minimized, the laser power of each pulse can be adjusted in response to feedback from a sensor at the treated tissue which can measure whether bonding has occurred. More computer simulations can be performed in a similar manner to that given above to determine the optimal laser pulse profile for different treatments given new parameters.

The foregoing description of preferred embodiments of the invention is presented for purposes of illustration and description and is not intended to be exhaustive or to limit the invention to the precise form disclosed. Many modifications and variations are possible in light of the above teaching.

The invention claimed is:

1. A method for intraluminal tissue welding in the anastomosis of a hollow organ, comprising:

providing a retractable catheter assembly including a catheter with at least one inflatable balloon and an optical fiber connected to the catheter, and a deployable biocompatible patch mounted on the balloon;

positioning the catheter assembly in a hollow organ adjacent to sections of the hollow organ to be joined;

positioning at least one balloon between the sections to be joined, inflating the balloon, thereby holding the sections together on the inflated balloon and deploying the patch against the inner wall of the hollow organ where the sections join; and forming a continuous hollow organ by delivering laser radiation through the optical fiber to the patch to bond the patch to the hollow organ, wherein the laser radiation has a pulse length that is within a factor of two of the time for laser energy to diffuse across a region over which the laser energy is deposited.

2. The method recited in claim 1, further comprising providing the catheter assembly with the patch circumferentially positioned around the balloon so that the patch is deployed upon inflation of the balloon.

3. The method recited in claim 1, further comprising providing the patch with a layer of light-absorbing dye on the side of the patch being bonded to the inner wall of the organ.

4. The method recited in claim 1, further comprising providing the patch with a bonding agent that strengthens the bond to the inner wall of the organ.

5. The method recited in claim 1, further comprising providing the patch with a material that polymerizes upon exposure to the laser radiation to form a mechanical bond to the inner wall of the hollow organ.

6. The method recited in claim 1, further comprising selecting a pulse structure for the laser radiation having a delay time between pulses that is within a factor of two of the time needed for a heated region over which the laser energy is deposited to cool.

7. The method as recited in claim 1, further comprising selecting a pulse structure for the laser radiation having a pulse length that minimizes the total treatment time needed to weld the patch to the organ wall and limits the thickness of a heated region over which the laser energy is deposited to less than about 100 μm.

8. The method as recited in claim 1, further comprising selecting a deployable biocompatible patch having a thickness that is about the thickness of a heated region over which the laser energy is deposited.

9. A method for intraluminal tissue welding in the anastomosis of a hollow organ, comprising:

providing a retractable catheter assembly including a catheter with at least one inflatable balloon and an optical fiber connected to the catheter;

positioning the catheter assembly in a hollow organ adjacent to sections of the hollow organ to be joined;

positioning at least one balloon between the sections to be joined and inflating the balloon, thereby holding the sections together on the inflated balloon; and forming a continuous hollow organ using a light-absorbing material applied to the sections that are to be joined together by applying laser radiation through the optical fiber to the light absorbing material, wherein the laser radiation has a pulse length that is within a factor of two of the time for laser energy to diffuse across a region over which the laser energy is deposited.

10. A method as recited in claim 9, wherein the laser radiation has a delay time between pulses that is within a factor of two of the time needed for the heated region over which the laser energy is deposited to cool.

11. The method as recited in claim 9, wherein the pulse length minimizes the total treatment time needed to weld the patch to the organ wall and limits the thickness of a heated region over which the laser energy is deposited to less than about 100 $\mu$m.

12. A method as recited in claim 9, further comprising a deployable biocompatible patch mounted on at least one balloon that is deployed upon inflation of the balloon against the inner wall of the hollow organ.

13. A method as recited in claim 9, further comprising providing the patch with a layer of light-absorbing dye on the side of the patch being bonded to the inner wall of the organ.

14. The method as recited in claim 9, further comprising selecting the patch to have a thickness that is about the thickness of a heated region over which the laser energy is deposited.

15. A method for intraluminal tissue welding for anastomosis of a hollow organ, comprising:

providing a retractable catheter assembly including a catheter with at least two inflatable balloons and an optical fiber connected to the catheter, and at least two deployable biocompatible patches mounted on the balloons;

positioning the catheter assembly in a hollow organ adjacent to severed free ends of the hollow organ;

positioning a graft between the free ends;

positioning the balloons between the free ends and the graft and inflating the balloons, thereby holding the free ends and the graft together on the inflated balloons and deploying the patches against the inner walls of the hollow organ and the graft where the ends join; and forming a continuous passageway through the hollow organ by bonding the patches to the hollow organ and the graft by delivering laser radiation through the optical fiber to the patches, wherein the laser radiation has a pulse length that is within a factor of two of the time for laser energy to diffuse across a region over which the laser energy is deposited.

* * * * *